United States Patent
Judge et al.

(10) Patent No.: US 10,101,269 B2
(45) Date of Patent: Oct. 16, 2018

(54) ESTIMATION OF WATER INTERFERENCE FOR SPECTRAL CORRECTION

(71) Applicant: Smiths Detection Inc., Edgewood, MD (US)

(72) Inventors: Kevin Judge, Southington, CT (US); Greger Andersson, Oxford, CT (US); Peng Zou, Ridgefield, CT (US)

(73) Assignee: SMITHS DETECTION INC., Edgewood, MD (US)

( * ) Notice: Subject to any disclaimer, the term of this patent is extended or adjusted under 35 U.S.C. 154(b) by 1045 days.

(21) Appl. No.: 14/446,473

(22) Filed: Jul. 30, 2014

(65) Prior Publication Data

US 2016/0033394 A1    Feb. 4, 2016

(51) Int. Cl.
| | |
|---|---|
| G01C 19/00 | (2013.01) |
| G01C 25/00 | (2006.01) |
| G01D 18/00 | (2006.01) |
| G01F 25/00 | (2006.01) |
| G06F 19/00 | (2018.01) |
| G01N 21/3504 | (2014.01) |
| G01N 21/35 | (2014.01) |

(52) U.S. Cl.
CPC ......... *G01N 21/3504* (2013.01); *G06F 19/70* (2013.01); *G01N 2021/3545* (2013.01); *G01N 2021/3595* (2013.01)

(58) Field of Classification Search
CPC ... G01N 2021/3545; G01N 2021/3595; G01N 21/3504; G06F 19/70
See application file for complete search history.

(56) References Cited

U.S. PATENT DOCUMENTS

| | | |
|---|---|---|
| 6,610,982 B2 | 8/2003 | Hoult |
| 6,662,116 B2 | 12/2003 | Brown |
| 6,687,620 B1 * | 2/2004 | Haaland ............... G01N 21/274 702/22 |

(Continued)

FOREIGN PATENT DOCUMENTS

EP              15068 A1 *    9/1980

OTHER PUBLICATIONS

International Preliminary Report on Patentability dated Feb. 9, 2017 for International Appln. No. PCT/US2015/042928.
Bruun, Susanne W. et al., "Correcting Attenuated Total Reflection Fourier Transform Infrared Spectra for Water Vapor and Carbon Dioxide", Applied Spectroscopy, 2006, vol. 60, Issue 9, pp. 1029-1039.
Fei, Wang et al., "Face recognition using spectral features", Pattern Recognition, Oct. 2007, vol. 40, Issue 10, pp. 2786-2797.

(Continued)

*Primary Examiner* — David M Gray
*Assistant Examiner* — Geoffrey T Evans
(74) *Attorney, Agent, or Firm* — Kevin E. West; Advent, LLP (57) ABSTRACT

A method includes decomposing a training set to obtain a principal component matrix having a plurality of principal component vectors. The method also includes variably rejecting portions of a sample spectrum vector that do not correspond to a selected one of the plurality of principal component vectors by incrementally providing a coefficient indicative of the weighting of the selected principal component vector for selected sub-regions. A corrected spectrum vector can be obtained by excluding certain sub-regions of the sample spectrum vector and corresponding principal component vector, multiplying the sample spectrum vector with the principal component matrix for non-excluded sub-regions, providing a predicted interference vector, and subtracting the predicted interference vector from the sample spectrum vector.

20 Claims, 5 Drawing Sheets

(56) References Cited

U.S. PATENT DOCUMENTS

| | | | |
|---|---|---|---|
| 2003/0023148 A1 | 1/2003 | Lorenz et al. | |
| 2003/0195708 A1* | 10/2003 | Brown | G01N 21/35 702/22 |
| 2005/0183958 A1 | 8/2005 | Wikiel et al. | |
| 2005/0285023 A1* | 12/2005 | Liu | G01N 21/274 250/221 |
| 2007/0142720 A1* | 6/2007 | Ridder | A61B 5/14532 600/336 |
| 2008/0112853 A1 | 5/2008 | Hall | |
| 2011/0184683 A1 | 7/2011 | Soller et al. | |
| 2012/0065948 A1 | 3/2012 | Tan et al. | |
| 2012/0318982 A1 | 12/2012 | Janik et al. | |
| 2014/0003561 A1* | 1/2014 | Ranson | H04B 1/109 375/346 |

OTHER PUBLICATIONS

Borchman, Douglas et al., "Changes in human meibum lipid with meibomian gland dysfunction using principal component analysis", Experimental Eye Research 91 (2010) 246-256.
Perkins, Jonathan H. et al., "The use of principal component analysis for the structural interpretation of mid-infrared spectra", 8386 Chemometrics and Intelligent Laboratory Systems, 15 (May 1992), No. 1, 75-86.
Extended European Search Report dated Mar. 7, 2018 for EP Appln. No. 15827708.7.

* cited by examiner

FIG. 5 though in applications the score can be assimilated to a concentration, P represents loadings, or spectra for each factor (analogous to pure component spectra), and the superscript $T$ denotes a matrix transpose.

ESTIMATION OF WATER INTERFERENCE FOR SPECTRAL CORRECTION

BACKGROUND

Generally, infrared (IR) spectroscopy (which is broadly defined herein to include, but is not necessarily limited: to near-infrared (NIR), mid-infrared (MIR), and far-infrared (FIR)) is based on molecular vibration and rotation modes, as well as combination and overtone bands. Because molar absorptivity in the near-infrared (NIR) region of the electromagnetic spectrum can be quite small, NIR radiation can typically penetrate quite far into a sample (e.g., as compared to mid-infrared (MIR) radiation). Thus, IR spectroscopy techniques, such as diffuse reflectance NIR spectroscopy and Fourier transform infrared spectroscopy (FTIR), can be useful for probing bulk material. Further, NIR spectroscopy generally requires limited or no sample preparation. Near-infrared spectroscopy (NIRS) can be used in materials characterization and molecular analysis applications as diverse as pharmaceuticals, medical diagnostics, neurology, neuroimaging, neonatal research, urology, food and agrochemical quality control, combustion product analysis, sports medicine, sports science, sports training, ergonomics, rehabilitation, and so forth.

SUMMARY

Systems and techniques for sample detection using, for example, Fourier transform infrared spectroscopy (FTIR) systems are described. For instance, a method includes decomposing a training set to obtain a principal component matrix having a plurality of principal component vectors. The method also includes variably rejecting portions of a sample spectrum vector that do not correspond to a selected one of the plurality of principal component vectors by incrementally: selecting a sub-region of the sample spectrum vector and a corresponding sub-region of the selected principal component vector; and multiplying the selected sub-region of the sample spectrum vector with the corresponding sub-region of the selected principal component vector to provide a coefficient indicative of the weighting of the selected principal component vector for the selected sub-regions. The method also includes excluding sub-regions of the sample spectrum vector and corresponding principal component vector based on the incrementally provided coefficients, multiplying the sample spectrum vector with the principal component matrix for the non-excluded sub-regions to provide a weighting vector indicative of the contribution of the principal component matrix, multiplying the weighting vector by the principal component matrix to provide a predicted interference vector, and subtracting the predicted interference vector from the sample spectrum vector to provide a corrected spectrum vector.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures.

DETAILED DESCRIPTION

Figure 1:
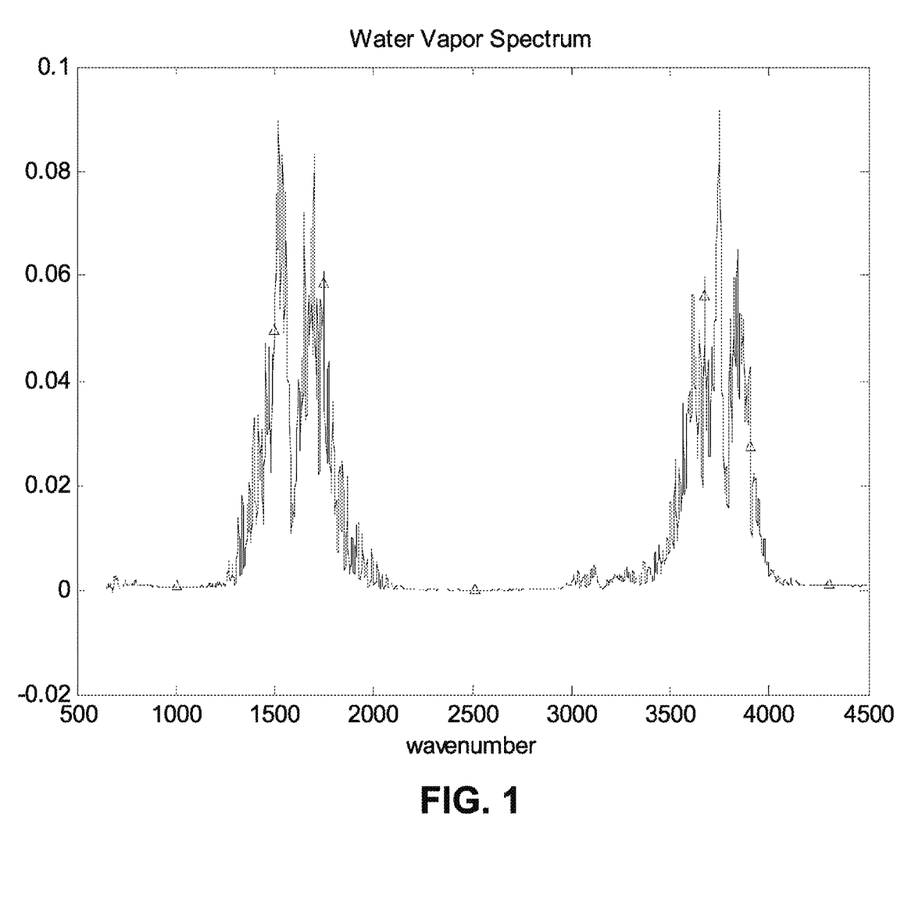
FIG. 1 is a graph of a Fourier transform infrared spectroscopy (FTIR) vapor phase spectrum of water vapor.

Optical spectrometry techniques, including infrared spectrometry, such as Fourier transform infrared spectroscopy (FTIR), can be implemented in detection tools used to verify the presence of particular analytes in samples, including, but not limited to dangerous or illicit materials (e.g., explosives, narcotics, biological toxins, chemical warfare agents, and the like). The presence or absence of certain analytes (e.g., as indicated by spectroscopic analysis) can be masked by the presence of interfering substances in a sample mixture. For example, water vapor can be a source of interference in FTIR vapor phase spectroscopy. A graph of an FTIR vapor phase spectrum of water vapor is shown in FIG. 1. Environmental factors, such as water vapor, can be present in a gas cell of quantitative analytic tools (e.g., spectrometers) and can appear as both positive and negative bands in a sample absorbance spectrum. Such factors can have a negative effect on the ability to identify and quantify library compounds. Over- or under-compensating for such environmental factors can similarly provide data outside of useful confidence intervals.

Techniques are described for obtaining an estimate of water absorbance in an FTIR vapor phase sample spectrum through variable selection. A training set of data is used to obtain a principal component matrix, which can be used to describe spectral patterns associated with water interference. The first principal component is determined over various ranges of narrow spectral regions, providing a plurality of values of the first principal component over the spectral range of interest. Spectral regions that provide a value for the first principal component that significantly differ from the other spectral regions can indicate an outlier value, which can signal that chemicals other than water can be present in those spectral regions. Removal of these outlier regions can provide a more accurate estimation of a coefficient or score assigned to each principal component, which, when applied to a full spectrum, can be used to estimate absorbance due to water vapor across the whole spectrum.

Principal component analysis (PCA) is a modeling technique used to identify major trends in a dataset. When applied to spectral data provided by spectroscopic analysis of a sample (such as water vapor), the factors/trends of that data can be determined for application to other samples to account for the presence/absence of the determined factors/trends. In an implementation, a principal component model is created using a training set of water vapor spectra measured at various temperatures and concentrations:

$$X_{train} = TP^T \quad (1)$$

where $X_{train}$ represents the training set of water vapor spectra, T represents a coefficient, or score, for each factor, and $P^T$ represents factors describing the spectral patterns associated with water interference (e.g., principal component loading vectors). The training set can include water vapor spectra measured at various temperatures and concentrations in order to capture a wide variety of environmental conditions in which a sample mixture can be found. Accordingly, the training set can be robust for the particular scenarios faced by a detection tool using the techniques described herein.

Figure 2:
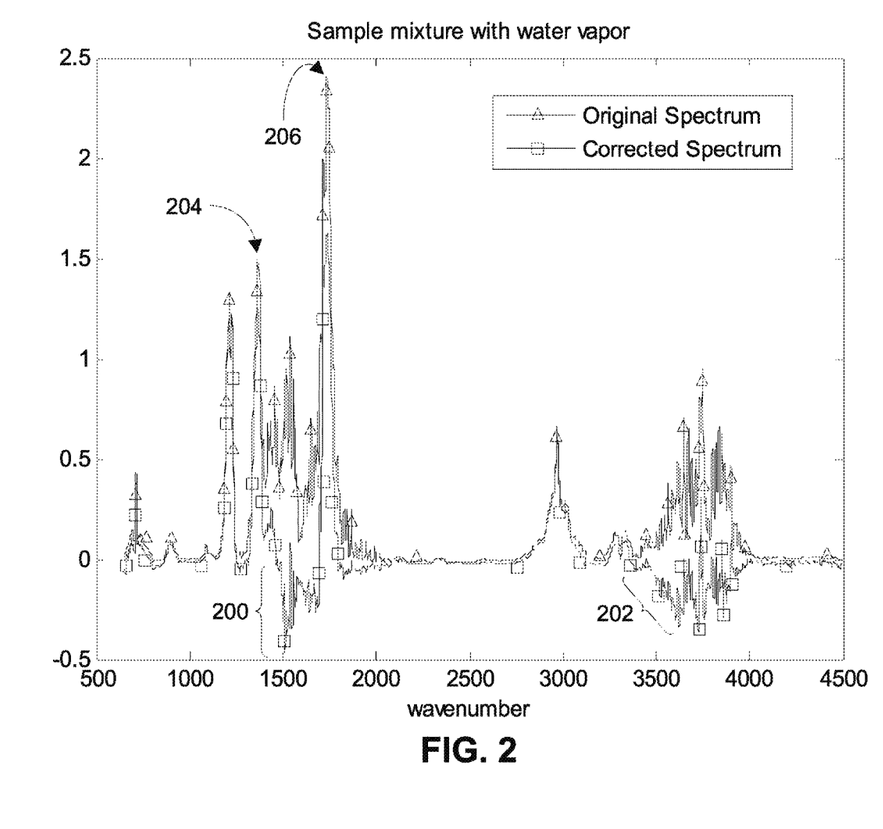
FIG. 2 is a graph of a spectrum for a sample mixture containing water, and a corrected spectrum having a correction for an amount of water vapor.

In applying the model to a sample data set, a coefficient, or score, is calculated for each factor:

$$X_{unknown} * P = T_{unknown} \quad (2)$$

where $X_{unknown}$ represents the sample spectral data set, P represents factors describing spectral patterns of the sample data set, and $T_{unknown}$ represents a calculated coefficient, or score, for each factor. These values can be used to correct a sample spectrum by removing a specific level of water vapor interference:

$$X_{corrected} = X_{unknown} - T_{unknown} * P^T \quad (3)$$

where $X_{corrected}$ represents the corrected sample spectrum that has been adjusted by removing the specific level of water vapor interference. FIG. 2 provide an example graph of a spectrum for a sample mixture containing water, and a corrected spectrum having a correction for an amount of water vapor provided in accordance with the above-described model. Where the sample spectrum includes other chemical peaks (i.e., non-water peaks) present in the water vapor region (e.g., as shown FIG. 1), then the corrected data set can provide an over-estimation or inaccuracy in the amount of water present, such as by indicating negative peaks. The graph provided in FIG. 2 shows at least two regions (shown at 200 and 202) having negative peaks. The remaining (positive) peaks can be affected with an over-estimation or inaccuracy of the amount of water vapor as well.

Figure 3:
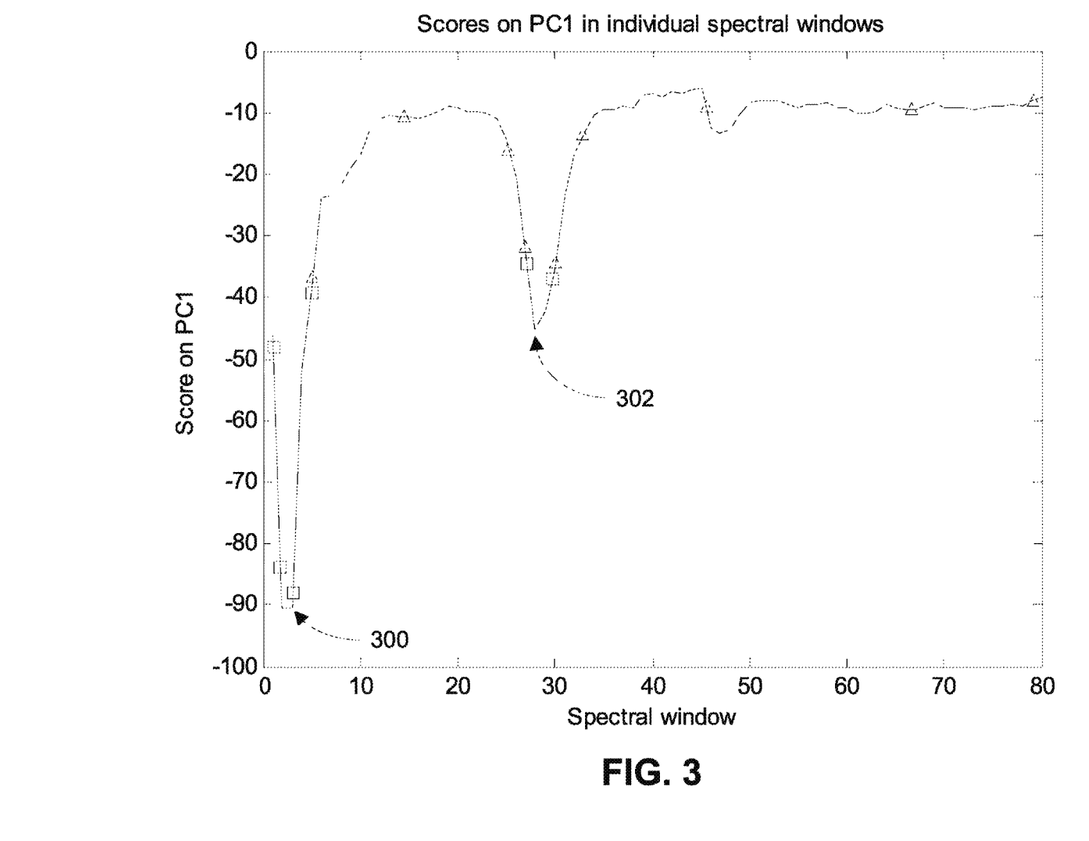
FIG. 3 is a graph of sliding window estimates of a first principal component in accordance with an example implementation of the present disclosure.

In implementations of the present disclosure, a sliding window method is used to identify spectral regions that contain features in addition to water vapor. Such a method can be utilized to avoid over-estimating or inaccurately providing the amount of water vapor present, particularly in situations where the sample includes chemical peaks (i.e., non-water peaks) present in the water vapor region. Similar to the PCA method described herein, a coefficient (T) is calculated for a first principal component (e.g., primarily a spectrum of water vapor) in a narrow spectrum region. The coefficient can be derived as a score matrix, such as by using the training set of water vapor spectra (e.g., a plurality of spectra taken over various concentrations and temperatures). In implementations, 45 $cm^{-1}$ (wavenumber) windows are used in steps of 10 $cm^{-1}$ to cover ranges of from about 1300 $cm^{-1}$ to about 2000 $cm^{-1}$ and from about 3400 $cm^{-1}$ to about 4000 $cm^{-1}$, which can correspond to the main peak regions of water vapor spectra (e.g., as shown in FIG. 1). Referring to FIG. 3, a graph of sliding window estimates of a first principle component is shown in accordance with an example implementation of the present disclosure is provided, where eighty (80) estimates of a score of the first component are included.

A threshold value of the score can be determined, where scores exceeding the threshold can indicate spectral regions that include chemical features other than water vapor. In implementations, a median value of the score is used as the threshold value, where spectral regions that include a score significantly different than the median can be flagged or documented as possibly containing features from chemicals present in the sample mixture other than water vapor.

Figure 4:
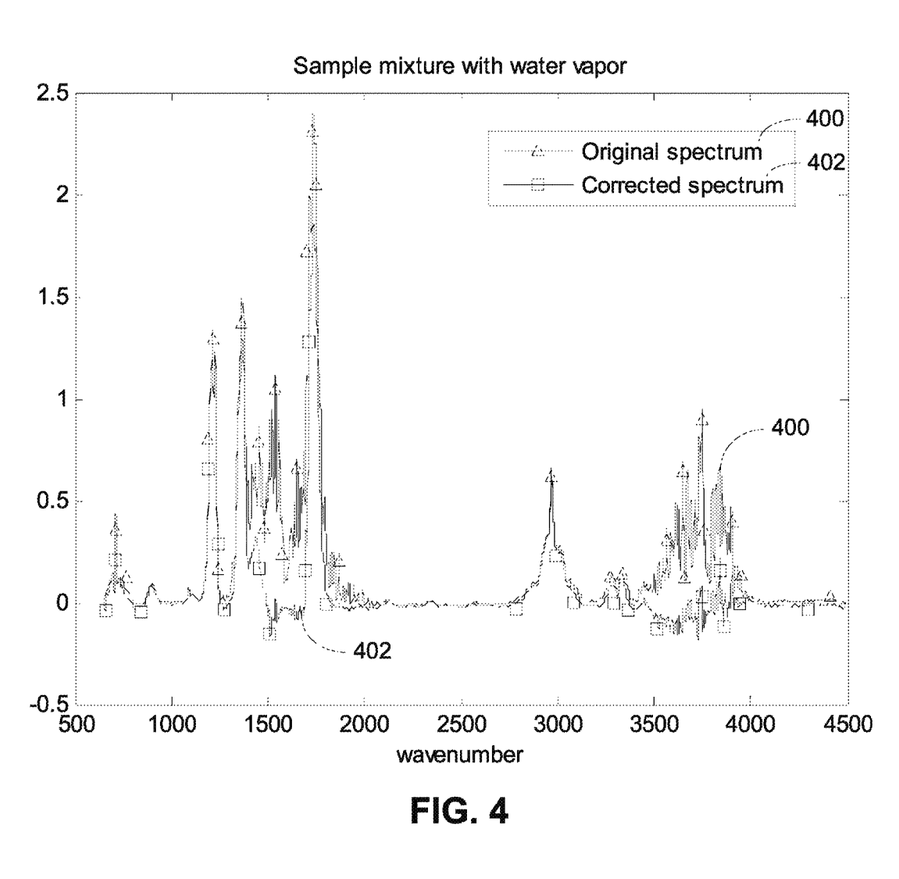
FIG. 4 is a graph of a spectrum for a sample mixture containing water, and a corrected spectrum having a correction for an amount of water vapor in accordance with an example implementation of the present disclosure.

As shown in the example implementation of FIG. 3, two regions spectral regions are shown (labeled 300 and 302) having significant different values than a median of the scores. These regions correspond to a peak associated with a chemical other than water. The region 300 is within the spectrum of from about 1300 $cm^{-1}$ to about 1400 $cm^{-1}$ (corresponding to windows 1-5). The region 302 is within the spectrum of from about 1700 $cm^{-1}$ to about 1775 $cm^{-1}$ (corresponding to windows 27-30). These regions correspond to the two strongest peaks (labeled as 204 and 206) within the first spectral region of interest in FIG. 2. Since these regions correspond to non-water chemicals, they can be removed from the model factors in order to provide an estimate of the contributions due to water in a sample. In implementations, the regions including a score that significant differs from the threshold value are removed from both the sample mixture spectrum and the original model factors (P) to obtain an updated estimation of the scores (e.g., more accurate), similar to equation (2) described herein. The updated estimation of the scores is then used with the original factors (of the full spectral range) to estimate the absorbance due to water vapor across the full spectrum. The absorbance due to water vapor is then subtracted from the sample mixture spectrum to provide the sample spectrum without substantial interference from water vapor. For example, FIG. 4 shows a graph of a spectrum for a sample mixture (labeled as 400) where the spectrum has interference due to the presence of water vapor. FIG. 4 also includes a corrected spectrum (labeled as 402) having a correction for an amount of water vapor in accordance with the sliding window method modifying the PCA model in an example implementation of the present disclosure. As can be seen in FIG. 4, the corrected spectrum 402 does provide the same level of over-estimation/inaccuracy of the amount of water vapor found in regions 200 and 202 of FIG. 2 as a result of the PCA method.

Figure 5:
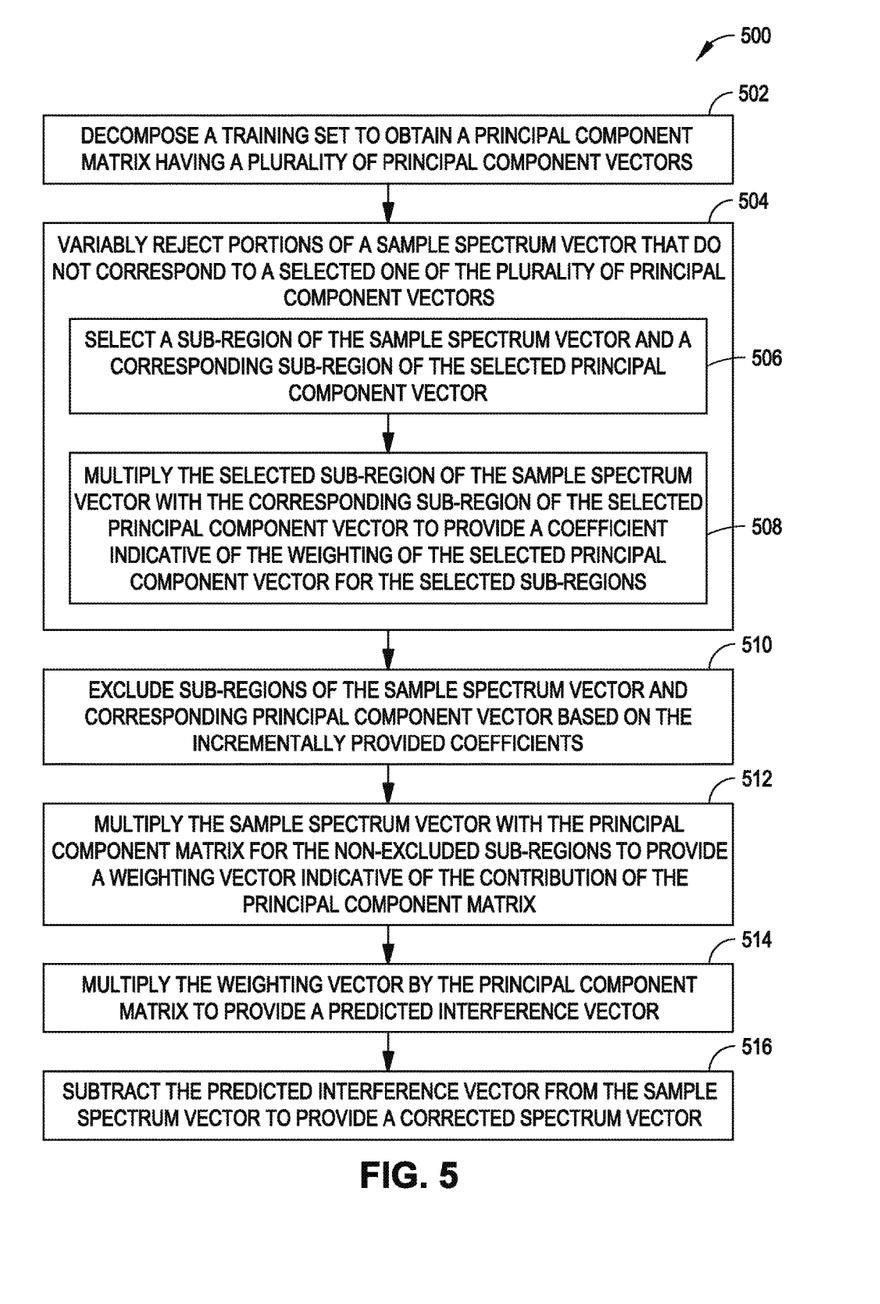
FIG. 5 is a flow diagram of a procedure for estimating water interference for FTIR spectrums and correcting for the presence of water in a sample mixture.

Referring now to FIG. 5, a flow diagram of a procedure 500 for estimating water interference for FTIR spectrums and correcting for the presence of water in a sample mixture is shown in accordance with an example implementation of the present disclosure. Aspects of the procedures described herein may be implemented in hardware, software, or a combination thereof The procedures are shown as a set of blocks that specify operations performed by one or more devices (e.g., IR spectroscopic instrumentation, a computer system controlling IR spectroscopic instrumentation or IR spectroscopic components) and are not necessarily limited to the order shown for performing the operations by the respective blocks. In implementations, aspects of the procedures described herein are implemented by fixed or mobile chemical detection systems, such as vapor phase detection systems.

Procedure 500 includes decomposing a training set to obtain a principal component matrix having a plurality of principal component vectors (Block 502). For example, a training set of water vapor spectra is decomposed to obtain a principal component matrix having a plurality of principal component vectors. In implementations, the training set includes water vapor spectra measured at various temperatures and concentrations.

Procedure 500 also includes variably rejecting portions of a sample spectrum vector (X) that do not correspond to a selected one of the plurality of principal component vectors ($P^T$) (Block 504). Block 504 includes an incremental progression of selecting a sub-region of the sample spectrum vector and a corresponding region of the selected principal component vector (Block 506) and multiplying the selected sub-region of the sample spectrum vector with the corresponding sub-region of the selected principle component vector to provide a coefficient indicative of the weighting of the selected principal component vector for the selected sub-regions (Block 508). For example, an implementation of coefficients indicative of the weighting of the selected principal component vector is shown in FIG. 3, where sliding window estimates of a first principle component is shown, where eighty (80) estimates of a score of the first component are included.

Procedure 500 also includes excluding sub-regions of the sample spectrum vector and corresponding principal component vector based on the incrementally provided coefficients (Block 510). For example, a threshold value of the score can be determined, where scores exceeding the threshold can indicate spectral regions that include chemical features other than water vapor. In implementations, a median value of the coefficients indicative of the weighting of the selected principal component vector is used as the threshold value, where spectral sub-regions that include a score significantly different than the median are excluded from the sample spectrum vector and corresponding principal component vector.

Procedure 500 further includes multiplying the sample spectrum vector with the principal component matrix for the non-excluded sub-regions to provide a weighting vector indicative of the contribution of the principal component matrix (Block 512). For example, in implementations the weighting vector (T) is provided according to the following:

$$T=X*P$$

where X represents the sample spectrum vector, and where P represents the principal component matrix for the non-excluded sub-regions. In implementations, T is provided by the following:

$$T=X*P*(P^T*P)^{-1}$$

where X represents the sample spectrum vector, P represents the principal component matrix for the non-excluded sub-regions, and $P^T$ represents the principal component matrix.

Procedure 500 further includes multiplying the weighting vector by the principal component matrix to provide a predicted interference vector (Block 514). For example, in implementations the predicted interference vector (X') is provided according to the following:

$$X'=T*P^T$$

where T represents the weighting vector, and $P^T$ represents the principal component matrix.

Procedure 500 further includes subtracting the predicted interference vector from the sample spectrum vector to provide a corrected spectrum vector (Block 516). For example, in implementations the corrected spectrum vector (E) is provided according to the following:

$$E=X-X'$$

where X represents the sample spectrum vector, and X' represents the predicted interference vector.

In implementations, the procedure 500 includes analyzing the corrected spectrum vector. For example, the corrected spectrum can be compared against a library of known spectra for various chemicals of interest in order to determine whether the corrected spectrum is associated with any of the chemicals of interest. After the analysis the procedure 500 can include activating one or more visual or audible indicia when the corrected spectrum is representative of a chemical of interest. For example, when it is determined that the corrected spectrum corresponds to or is associated with a chemical of interest, a chemical detection system can activate an audible or visible alarm, generate a visual output to a user-interface, and so forth.

It is to be noted that the foregoing described embodiments and implementations may be conveniently implemented using conventional general purpose digital computers programmed according to the teachings of the present specification, as will be apparent to those skilled in the computer art. Appropriate software coding may readily be prepared by skilled programmers based on the teachings of the present disclosure, as will be apparent to those skilled in the software art.

It is to be understood that the embodiments and implementations described herein may be conveniently implemented in forms of a software package. Such a software package may be a computer-readable storage medium having computer executable instructions or a computer program product which employs a non-transitory computer-readable storage medium including stored computer code which is used to program a computer to perform the disclosed functions and processes disclosed herein. The computer-readable storage medium may include, but is not limited to, any type of conventional floppy disk, optical disk, CD-ROM, magnetic disk, hard disk drive, magneto-optical disk, ROM, RAM, EPROM, EEPROM, magnetic or optical card, or any other suitable media for storing electronic instructions.

As used herein, the term "about" shall mean about and/or exactly with respect to the value or range of values specified. Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claims.

What is claimed is:

1. A method comprising:
   decomposing a training set corresponding to spectral data obtained for an interfering substance using an infrared spectrometry system to obtain a principal component matrix having a plurality of principal component vectors;
   generating a sample spectrum vector for a sample mixture using the infrared spectrometry system;
   variably rejecting portions of the sample spectrum vector that do not correspond to a selected one of the plurality of principal component vectors by incrementally:
   selecting a sub-region of the sample spectrum vector and a corresponding sub-region of the selected principal component vector; and
   multiplying the selected sub-region of the sample spectrum vector with the corresponding sub-region of the selected principal component vector to provide a coefficient indicative of the weighting of the selected principal component vector for the selected sub-regions;
   excluding sub-regions of the sample spectrum vector and corresponding principal component vector based on the incrementally provided coefficients;
   multiplying the sample spectrum vector with the principal component matrix for the non-excluded sub-regions to provide a weighting vector indicative of the contribution of the principal component matrix;
multiplying the weighting vector by the principal component matrix to provide a predicted interference vector, the predicted interference vector corresponding to the interfering substance in the sample mixture, the interfering substance being capable of masking a presence or an absence of one or more chemicals of interest in the sample mixture;
subtracting the predicted interference vector from the sample spectrum vector to provide a corrected spectrum vector; and
comparing the corrected spectrum vector to known spectrum data for one or more chemicals of interest to determine if the corrected spectrum vector is representative of a chemical of interest.

2. The method as recited in claim 1, further comprising measuring spectra of water vapor to obtain the training set, the water vapor serving as an interfering substance.

3. The method as recited in claim 2, wherein measuring spectra of water vapor includes measuring spectra of water under at least one of different temperatures or different pressures.

4. The method as recited in claim 1, further comprising removing spectral regions with values outlying a majority of the incrementally provided coefficients.

5. The method as recited in claim 1, wherein the weighting vector is equal to the sample spectrum vector times the principal component matrix for the non-excluded sub-regions times the inverse of (the principal component matrix times the principal component matrix for the non-excluded sub-regions).

6. The method as recited in claim 1, wherein excluding sub-regions of the sample spectrum vector and corresponding principal component vector based on the incrementally provided coefficients includes excluding sub-regions of the sample spectrum vector and corresponding principal component vector that are greater than a threshold value of the incrementally provided coefficients.

7. The method as recited in claim 6, wherein the threshold value of the incrementally provided coefficients is a median of the incrementally provided coefficients.

8. A method comprising:
decomposing a training set corresponding to spectral data obtained for an interfering substance using an infrared spectrometry system to obtain a principal component matrix having a plurality of principal component vectors;
generating a sample spectrum vector for a sample mixture using the infrared spectrometry system;
variably rejecting portions of the sample spectrum vector that do not correspond to a selected one of the plurality of principal component vectors by incrementally:
selecting a sub-region of the sample spectrum vector and a corresponding sub-region of the selected principal component vector; and
multiplying the selected sub-region of the sample spectrum vector with the corresponding sub-region of the selected principal component vector to provide a coefficient indicative of the weighting of the selected principal component vector for the selected sub-regions;
excluding sub-regions of the sample spectrum vector and corresponding principal component vector based on the incrementally provided coefficients;
multiplying the sample spectrum vector with the principal component matrix for the non-excluded sub-regions to provide a weighting vector indicative of the contribution of the principal component matrix;
multiplying the weighting vector by the principal component matrix to provide a predicted interference vector, the predicted interference vector corresponding to the interfering substance in the sample mixture, the interfering substance being capable of masking a presence or an absence of one or more chemicals of interest in the sample mixture;
subtracting the predicted interference vector from the sample spectrum vector to provide a corrected spectrum vector;
comparing the corrected spectrum vector to known spectrum data for one or more chemicals of interest to determine if the corrected spectrum vector is representative of a chemical of interest; and
activating one or more visual or audible indicia when the corrected spectrum is representative of a chemical of interest.

9. The method as recited in claim 8, further comprising measuring spectra of water vapor to obtain the training set, the water vapor serving as an interfering substance.

10. The method as recited in claim 9, wherein measuring spectra of water vapor includes measuring spectra of water under at least one of different temperatures or different pressures.

11. The method as recited in claim 8, further comprising removing spectral regions with values outlying a majority of the incrementally provided coefficients.

12. The method as recited in claim 8, wherein the weighting vector is equal to the sample spectrum vector times the principal component matrix for the non-excluded sub-regions times the inverse of (the principal component matrix times the principal component matrix for the non-excluded sub-regions).

13. The method as recited in claim 8, wherein excluding sub-regions of the sample spectrum vector and corresponding principal component vector based on the incrementally provided coefficients includes excluding sub-regions of the sample spectrum vector and corresponding principal component vector that are greater than a threshold value of the incrementally provided coefficients.

14. The method as recited in claim 13, wherein the threshold value of the incrementally provided coefficients is a median of the incrementally provided coefficients.

15. A computer-readable storage medium comprising code, the code comprising:
decomposing a training set corresponding to spectral data obtained for an interfering substance using an infrared spectrometry system to obtain a principal component matrix having a plurality of principal component vectors;
receiving a sample spectrum vector for a sample mixture using the infrared spectrometry system;
variably rejecting portions of the sample spectrum vector that do not correspond to a selected one of the plurality of principal component vectors by incrementally:
selecting a sub-region of the sample spectrum vector and a corresponding sub-region of the selected principal component vector; and
multiplying the selected sub-region of the sample spectrum vector with the corresponding sub-region of the selected principal component vector to provide a coefficient indicative of the weighting of the selected principal component vector for the selected sub-regions;

excluding sub-regions of the sample spectrum vector and corresponding principal component vector based on the incrementally provided coefficients;

multiplying the sample spectrum vector with the principal component matrix for the non-excluded sub-regions to provide a weighting vector indicative of the contribution of the principal component matrix;

multiplying the weighting vector by the principal component matrix to provide a predicted interference vector, the predicted interference vector corresponding to the interfering substance in the sample mixture, the interfering substance being capable of masking a presence or an absence of one or more chemicals of interest in the sample mixture;

subtracting the predicted interference vector from the sample spectrum vector to provide a corrected spectrum vector; and comparing the corrected spectrum vector to known spectrum data for one or more chemicals of interest to determine if the corrected spectrum vector is representative of a chemical of interest.

16. The computer-readable storage medium as recited in claim 15, further comprising code for measuring spectra of water vapor to obtain the training set, the water vapor serving as the interfering substance.

17. The computer-readable storage medium as recited in claim 16, wherein measuring spectra of water vapor includes measuring spectra of water under at least one of different temperatures or different pressures.

18. The computer-readable storage medium as recited in claim 15, further comprising code for removing spectral regions with values outlying a majority of the incrementally provided coefficients.

19. The computer-readable storage medium as recited in claim 15, wherein the weighting vector is equal to the sample spectrum vector times the principal component matrix for the non-excluded sub-regions times the inverse of (the principal component matrix times the principal component matrix for the non-excluded sub-regions).

20. The computer-readable storage medium as recited in claim 15, wherein excluding sub-regions of the sample spectrum vector and corresponding principal component vector based on the incrementally provided coefficients includes excluding sub-regions of the sample spectrum vector and corresponding principal component vector that are greater than a median of the incrementally provided coefficients.

* * * * *